United States Patent
Günther et al.

[11] Patent Number: 5,493,912
[45] Date of Patent: Feb. 27, 1996

[54] ULTRASONIC PROBE SUITABLE FOR ACOUSTIC COUPLING VIA A WATER CHANNEL

[75] Inventors: Werner Günther, Pulheim; Ulrich Sauer, Erftstadt-Lechenich, both of Germany

[73] Assignee: Krautkramer GmbH & Co., Germany

[21] Appl. No.: 196,262

[22] PCT Filed: May 7, 1992

[86] PCT No.: PCT/DE92/00374

§ 371 Date: Apr. 4, 1994

§ 102(e) Date: Apr. 4, 1994

[87] PCT Pub. No.: WO93/04362

PCT Pub. Date: Mar. 4, 1993

[30] Foreign Application Priority Data

Aug. 16, 1991 [DE] Germany .............................. 9110135 U

[51] Int. Cl.⁶ .................................................. G01N 29/28
[52] U.S. Cl. .................................................. 73/644
[58] Field of Search ........................... 73/644, 632, 629

[56] References Cited

U.S. PATENT DOCUMENTS

| | | | |
|---|---|---|---|
| 4,587,849 | 5/1986 | Gross | 73/644 |
| 4,726,231 | 2/1988 | Tretout et al. | 73/644 |
| 5,001,932 | 3/1991 | Light et al. | 73/644 |
| 5,123,281 | 6/1992 | Cox et al. | 73/644 |

*Primary Examiner*—Hezron E. Williams
*Assistant Examiner*—Rose M. Finley
*Attorney, Agent, or Firm*—Eckert Seamans Cherin & Mellott

[57] ABSTRACT

An ultrasonic probe suitable for acoustic-coupling via a water channel, includes a main element with a housing. Housed in watertight fashion in the housing is an ultrasonic oscillator, the oscillator being joined to a protective layer which is flush with the lower surface of the housing. The housing wall encloses a water channel which is connected at the input end to a hose connector and whose output end opens out in the lower surface next to the oscillator. The side wall of the housing immediately next to the lower surface has a physically interlocking coupling element for a nozzle with a matching physically interlocking coupling element to be fitted over the lower surface. The nozzle forms a truncated-conical channel which tapers towards its open end and which fits against the surface of the oscillator at the input end. The nozzle also has a blind-end bore, which forms an extension of the output end of the water channel, and a cross-channel between the blind-end bore and the channel in the nozzle. The nozzle is made of a material whose acoustic impedance is as close as possible to that of water.

14 Claims, 1 Drawing Sheet

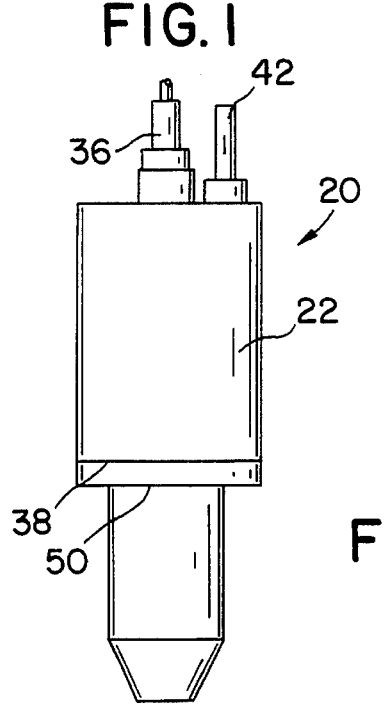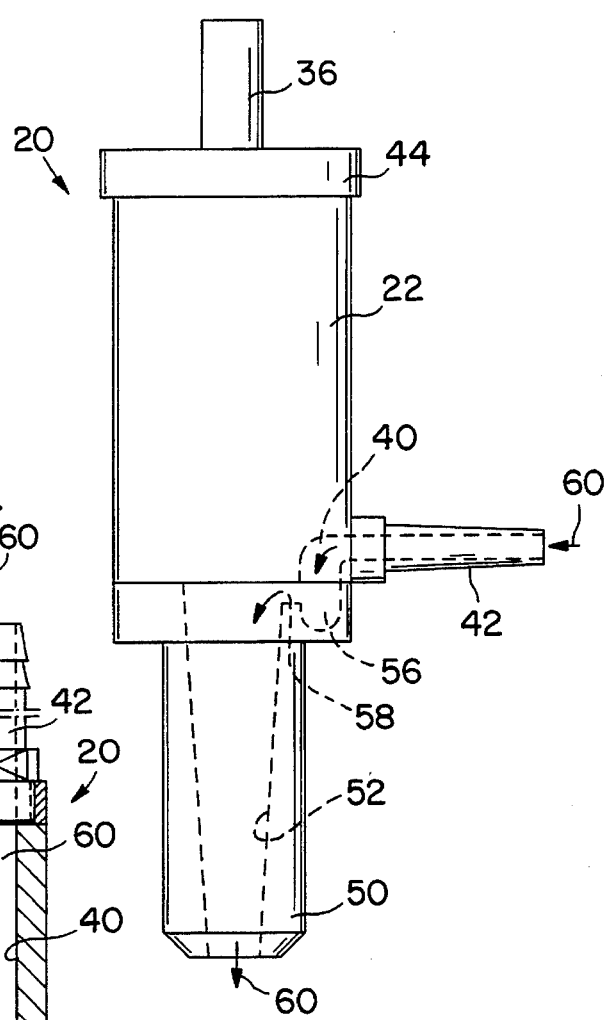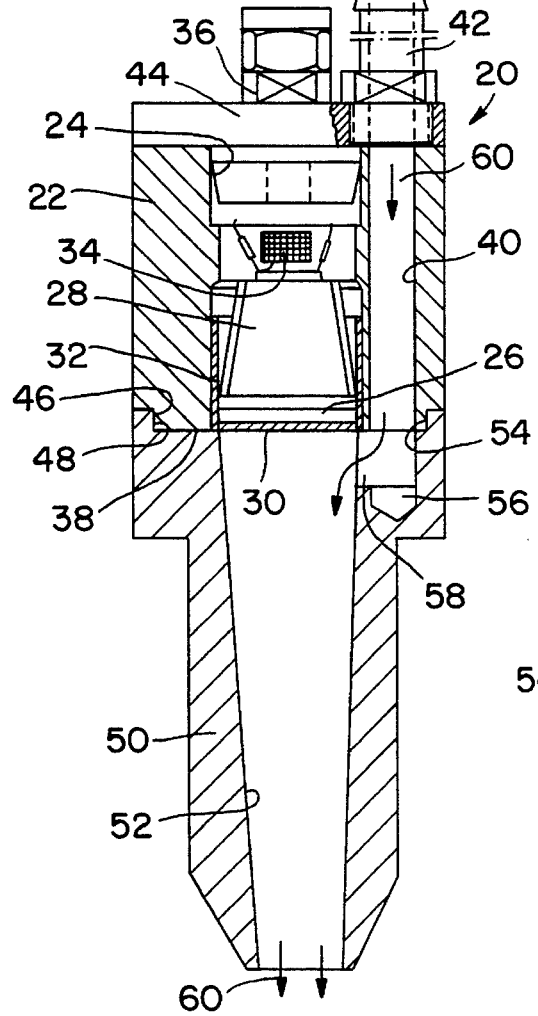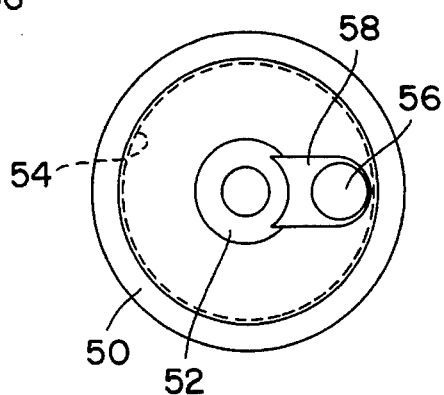

ULTRASONIC PROBE SUITABLE FOR ACOUSTIC COUPLING VIA A WATER CHANNEL

The invention relates to an ultrasonic probe suitable for acoustic coupling through a water lead section and having of a main part having an enclosure in which an ultrasonic crystal is housed, the ultrasonic crystal being connected to a protective layer the limits of which lie flush with a lower surface of the enclosure.

As far as ultrasonic probes of the aforementioned type are concerned, general reference is made to the German book "Werkstoffprufung mit Ultraschall" (Ultrasonic Testing of Materials) by J. and H. Krautkramer, 4th edition, Springerverlag.

Ultrasonic probes are probes ready for service for ultrasonic testing of workpieces. For the performance of testing the probes are connected to a suitable ultrasonic instrument. According to prior art, different probes are employed according to the acoustic coupling of the probe to the workpiece, for example for acoustic coupling by the immersion method, the semi-immersion method, by water jet or other means of acoustic coupling, for example sliding contact, contact through a pasty mass, etc. The fact that state of the art ultrasonic probes are not suitable for all methods of acoustic coupling is however a disadvantage for practical application of an ultrasonic probe. In consequence, different probes must be employed according to the method of acoustic coupling. The user, however, wishes to be able to apply all methods of acoustic coupling with a single ultrasonic probe. It is particularly advantageous for practical application if an ultrasonic probe can be converted from a probe for acoustic coupling through a water gap to a probe for acoustic coupling through a water jet without the ultrasonic probe having to be changed.

This is where the invention comes in. Its object is to provide an ultrasonic probe which can be employed universally for different types of acoustic coupling to a workpiece.

Taking as a basis the ultrasonic probe described initially, the object is achieved by means of an ultrasonic probe with the characteristics of claim 1.

This ultrasonic probe can be employed without flowing water being fed through its water channel, for example for testing by the immersion method or by acoustic coupling through a pasty mass. It can however also be employed for acoustic coupling with water gap, in which case flowing water is fed through its water channel. If the nozzle part is fitted to the positive-locking coupling facility, the ultrasonic probe immediately becomes suitable for acoustic coupling through a water jet. The entire range of possible acoustic coupling methods can therefore be covered by a single ultrasonic probe. In practice, this results in savings in time and expenditure. Moreover, the reliability of the measuring results is increased for the less experienced user, as there is no need for the user to make adjustment for differences in sonic response between different probes with corresponding adaptation of the ultrasonic instrument.

Since the protective layer, with which the ultrasonic crystal is sealed off underneath, lies flush with the lower surface of the enclosure of the main part, the ultrasonic probe according to the invention can be applied with sliding contact along a workpiece. The ultrasonic probe is likewise suitable for acoustic coupling through an externally applied water film or through a paste. The water channel is always employed when water is to be introduced into the region of acoustic coupling through the ultrasonic probe according to the invention. Without the nozzle part, water can for example be fed in through the probe for water gap acoustic coupling or in order to maintain the workpiece semi-immersed in the case of acoustic coupling by means of the semi-immersion method. With the nozzle part fitted, practical use of the water jet acoustic coupling method is possible. The blind hold prevents turbulences and air bubbles, even in unfavorable working situations. The blind hole serves as a baffle hold. The cross-section of the transverse channel is dimensioned such that with the specified water flow through the water channel, the nozzle channel is completely filled and a water jet is formed.

Since the nozzle part is manufactured from a material the acoustic impedance of which is as close as possible to the acoustic impedance of water, the spurious echos from the lateral delimitations are kept low. The conical frustum shape of the nozzle part is adapted to the shape of the ultrasonic beam of the ultrasonic crystal. The 20 dB ultrasonic beam limit or another common ultrasonic beam limit (e.g. 3 or 6 dB) can for example be employed as its delimitation. This results in the quantity of liquid per time unit required for acoustic coupling being kept low.

Acrylic glass, epoxy resin and polythene have in particular probes to be suitable materials for the nozzle part. The length of the conical frustum shaped nozzle channel is determined in accordance with prior art, being adapted for example to the near-field length, i.e., the distance between the transducer and the region of maximum focusing.

In a preferred further development, the enclosure is essentially cylindrical. Again preferably the water channel should run parallel to the cylinder axis in this case. Manufacture of the enclosure as a whole is simplified as a result.

Disk-shaped ultrasonic crystals are particularly preferable. The shape of the enclosure is simplified as a result, and, in particular, the ultrasonic crystal is adapted optimally to the truncated frustum-shaped nozzle channel.

Further advantages and characteristics of the invention arise from the further claims and in the description below of embodiments, not to be regarded as restrictive, which are explained in greater detail with reference to the drawing. The drawing shows in:

FIG. 1 a side view of an ultrasonic probe with main part and nozzle part;

FIG. 2 an axial section through an ultrasonic probe similar to FIG. 1;

FIG. 3 a side view similar to FIG. 1 of a further embodiment of an ultrasonic probe;

FIG. 4 a top view of the nozzle section of the embodiment as per FIG. 3.

The ultrasonic probe according to the invention consists of a main part 20 having in the embodiments per FIG. 1 and FIG. 2 a cylindrical enclosure 22. The enclosure 22 has a centric, slightly stepped location hole 24 for a disk shaped ultrasonic crystal 26. An attenuator 28 of conical frustum shape is cemented onto the rear of the crystal, and the front, which faces down, has a protective layer 30 of metal (or, in another embodiment, of plastic). The unit comprising the ultrasonic crystal 26, attenuator 28 and protective layer 30 is located within a centering ring 32, which is inserted into the location hole 24. The ultrasonic crystal 26 is connected electrically in a well-known manner: the electrical supply lines are connected to a soldering terminal above the attenuator and are drawn in visibly. An electrical adapter 34 is located between them. The electrical terminals are connected to a plug, connector 36 of waterproof construction. The limits of the protective layer 30 underneath, which is manufactured of steel, lie flush with a lower surface 38 of the enclosure.

A water channel 40 is located in the enclosure 22 parallel to the central axis of the cylindrical enclosure 22. The water channel is fitted with a hose connection 42 on the inlet side, i.e. at the top in the diagrams, and opens out in the lower surface 38 and immediately adjacent to the protective layer 30 on the outlet side.

The enclosure 22 is closed off at the top by a cover 44. The cover 44 and enclosure 22 have a combined length of 46 mm and a diameter of 45 mm.

A step 46 is formed on the lower end of the cylindrical wall of the enclosure 22 and immediately adjoining the lower surface 38. A thread 48 is provided on the step and forms a positive-locking coupling facility for the nozzle part described below.

The nozzle part 50 is manufactured from acrylic glass. The inside of the nozzle part forms a centric, truncated cone-shaped nozzle channel 52. At its upper inlet area the diameter of the nozzle part corresponds exactly to the diameter of the ultrasonic crystal 26, i.e, 20 mm, and narrows downwards over a total length of 80 mm to an inside diameter of 12 mm.

The nozzle part 50, which is essentially a turned part, has in its upper end region a projection adapted to the step 46, the projection having an internal thread which in this instance forms a coupling facility matching the coupling facility 48. The nozzle part 50 and the main part 20 are connected in the manner shown by the parts 48 and 54 such that the upper side of the nozzle part 50 sits closely on the lower surface 38. The joint is watertight.

The exterior shape itself of the nozzle part 50 is as desired. In the embodiment shown, the case is cylindrical, stepped, and of truncated cone shape in its lower part.

A blind hole 56 is formed in the nozzle part 50 as a direct ,extension of the water channel 40. The blind hole is connected to the nozzle channel 52 by a transverse channel 58. The nozzle channel is integrated into the nozzle part 50 from the latter's upper side, and is not as deep as the blind hole 56, so that part of the blind hole, approximately 5 mm in the embodiment, remains as a baffle hole. The blind hole may terminate flat or in a point; it prevents turbulence and air bubbles from occurring, even in unfavorable situations. The cross-section of the transverse channel 58 is dimensioned such that the nozzle channel 52 is completely filled under the specified water flow, and a free, clearly delimited water jet forms at this outlet end.

The course of water flow through the entire ultrasonic probe is shown diagrammatically by arrows 60.

The third embodiment as per FIGS. 3 and 4 corresponds essentially to the embodiment already discussed. There is however an essential difference in that the water channel 40 runs in an L-shape and is as short as possible in design; the hose connection 42 projects radially away from the enclosure 22 and is immediately adjacent to the lower surface 38. The nozzle channel 52, which narrows downwards, can be seen in FIG. 4, as can the internal thread 48. The transverse channel 58, which connects the blind hole 56 with the nozzle channel 52, has an axial length of 7.5 mm and a width of 10.5 mm. The blind hole 56 and therefore also the water channel 40 have a diameter of 7 mm. The inlet diameter of the nozzle channel 52 is likewise 20 mm, narrowing downwards to 12.2 mm.

The coupling facility 48 and the matching coupling facility 54 may also differ in design from the embodiments described, for example by having a bayonet fixing. The decisive factor in the design of this facility 48, 54 is that when the main part 20 and the nozzle part 50 are coupled, the blind hole 56 and the water channel 40 are aligned exactly. This can be checked if necessary by markings provided on the outside of the outer case of parts 22 and 50. In the coupled condition, the markings must align.

We claim:

1. An ultrasonic probe for acoustic coupling through a water lead section, comprising:

a main part formed with a water tight enclosure for housing an ultrasonic crystal having a diameter, the enclosure having at least one side wall and a lower surface;

a protective layer connected to the ultrasonic crystal, the protective layer being flush with the lower surface of the enclosure;

a water channel positioned adjacent to the ultrasonic crystal, the water channel having an inlet with a hose connection and an outlet which opens out on the lower surface of the enclosure;

a positive locking coupling facility located on the side wall immediately adjoining the lower surface of the enclosure; and, a nozzle part for water-jet acoustic coupling, the nozzle part: having an inlet end with a matching positive-locking coupling facility and a free end, the inlet end of the nozzle part being coupled to the lower surface of the enclosure by the positive locking coupling facility and the matching positive-locking coupling facility, the nozzle being formed with a conical frustum shaped nozzle channel extending between the inlet end and the free end, the channel having a diameter equal to the diameter of the ultrasonic crystal at the inlet end, the channel narrowing to the free end of the nozzle, the nozzle part being formed with a blind hole extending the outlet of the water channel, the blind hole connecting the water channel to the nozzle channel by a transverse channel, the nozzle being manufactured from a material with an acoustic impedance as close as possible to the acoustic impedance of water.

2. The ultrasonic probe according to claim 1, wherein the enclosure is essentially cylindrical.

3. The ultrasonic probe according to claim 2, wherein the housing has a housing axis and the water channel runs parallel to the housing axis.

4. The ultrasonic probe according to claim 1, wherein the ultrasonic crystal is disk-shaped.

5. The ultrasonic probe according to claim 2, wherein the ultrasonic crystal has an axis arranged on the housing axis.

6. The ultrasonic probe according to claim 1, wherein the protective layer is metallic and the ultrasonic crystal is connected to the protective layer.

7. The ultrasonic probe according to claim 1, wherein the main part and the nozzle part are flush in the area of the positive locking coupling facility.

8. The ultrasonic probe according to claim 1, wherein the cross-section of the transverse channel is greater than the cross-section of the water channel and smaller than the cross-section of the nozzle, channel at the free end of the nozzle.

9. The ultrasonic probe according to claim 1, wherein the diameter of the blind hole and the diameter of the water channel are identical.

10. The ultrasonic probe according to claim 1, wherein the diameter of the water channel is smaller, at least by a factor of 2, than the diameter of the nozzle channel at the free end of the nozzle.

11. The ultrasonic probe according to claim 1, wherein the cross-section of the transverse channel is greater, at least by a factor of 2, than the cross-section of the water channel.

12. The ultrasonic probe according to claim 1, wherein the nozzle part is manufactured from at least one of acrylic glass, epoxy resin, and polythene, and is constructed from a single-piece.

13. The ultrasonic probe according to claim 4 characterized in that the ultrasonic crystal (26) is arranged with its axis on the cylinder axis.

14. The Ultrasonic probe according to claim 6, wherein the protective layer is made of steel.

* * * * *